United States Patent [19]

Lonneman et al.

[11] Patent Number: 5,368,563

[45] Date of Patent: Nov. 29, 1994

[54] SPRAYER ASSEMBLY FOR PHYSIOLOGIC GLUE

[75] Inventors: Alan Lonneman, Plymouth; Curtis H. Miller, Burnsville, both of Minn.

[73] Assignee: Micromedics, Inc., Eagan, Minn.

[21] Appl. No.: 149,151

[22] Filed: Nov. 8, 1993

Related U.S. Application Data

[63] Continuation of Ser. No. 809,885, Dec. 18, 1991, abandoned.

[51] Int. Cl.[5] .................................. A61M 37/00
[52] U.S. Cl. ............................... 604/82; 604/191; 239/404; 239/543
[58] Field of Search .................. 604/82, 88, 94, 187, 604/191, 218, 310, 311; 239/404, 418, 468, 543, 490, 463, 303, 304, 306; 222/137

[56] References Cited

U.S. PATENT DOCUMENTS

| | | | |
|---|---|---|---|
| 713,017 | 11/1902 | Pumphrey | 239/463 |
| 1,614,532 | 1/1927 | Mobley | 128/200.23 |
| 2,747,936 | 5/1956 | Wahlin | 239/490 |
| 3,236,457 | 2/1966 | Kennedy et al. | 239/304 |
| 3,269,389 | 8/1966 | Meurer et al. | 604/191 |
| 3,416,737 | 12/1968 | Venus, Jr. | 239/490 |
| 3,942,725 | 3/1976 | Green | 239/468 |
| 3,945,574 | 3/1976 | Polnauer et al. | 239/404 |
| 4,040,420 | 8/1977 | Speer . | |
| 4,109,653 | 2/1977 | Kozam . | |
| 4,359,049 | 11/1982 | Redl . | |
| 4,631,055 | 12/1986 | Redl et al. . | |
| 4,735,616 | 4/1988 | Eibl et al. . | |
| 4,826,048 | 5/1989 | Skorka et al. | 604/191 |
| 4,874,368 | 10/1989 | Miller et al. . | |
| 4,902,281 | 2/1990 | Avoy | 604/191 |
| 4,987,336 | 12/1990 | Capozzi et al. . | |
| 5,116,315 | 5/1992 | Copozzi et al. | 604/82 |

Primary Examiner—John D. Yasko
Assistant Examiner—Anthony Gutowski
Attorney, Agent, or Firm—Kinney & Lange

[57] ABSTRACT

An improved sprayer assembly for delivery of physiologic glue, including fibrin glue, is disclosed. The sprayer assembly is comprised of at least one female receptacle rigidly affixed to a base member and a sprayer member having at least one atomizing ejection port on an external surface opposing the base member. Within the sprayer member, a system of fluid channels permits each reservoir to be emptied into a well from angular connecting channels, which causes enhanced turbulence within each well. A vortex is created which propagates through an exit port and down an exit channel, causing each solution to exit the sprayer member at each ejection port in a swirling pattern. The spray patterns emitted from each syringe or reservoir overlap, causing droplets of solution to contact one another and commence a clotting reaction at a wound surface.

The sprayer assembly is joined to a conventional syringe, a catheter or other solution reservoir. Thus, quickly reacting substances are stored apart from one another and only come into contact while airborne. The positioning of the ejection ports is selected to prevent droplets exiting one port from contaminating the contents within the neighboring port and channel. Thus, propagation of the reaction within the device, and subsequent plugging of the assembly is avoided.

21 Claims, 2 Drawing Sheets

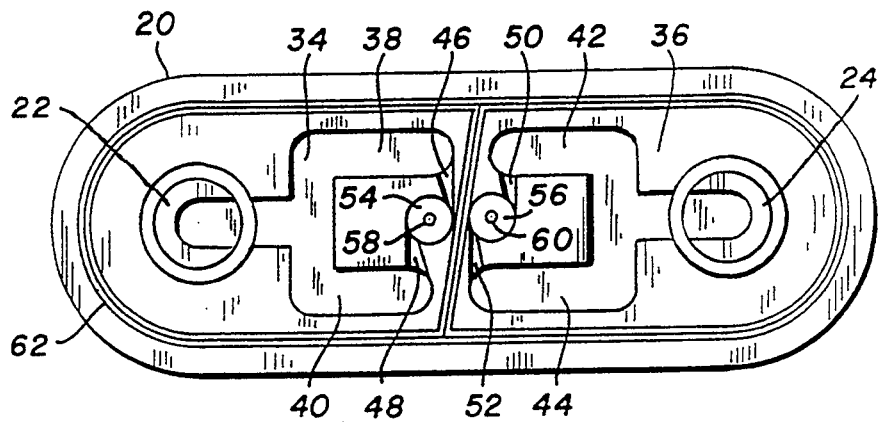
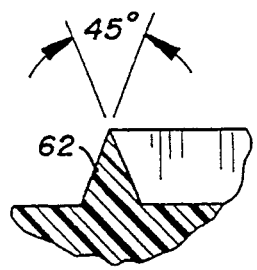
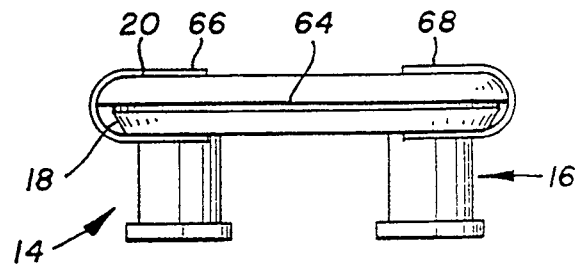
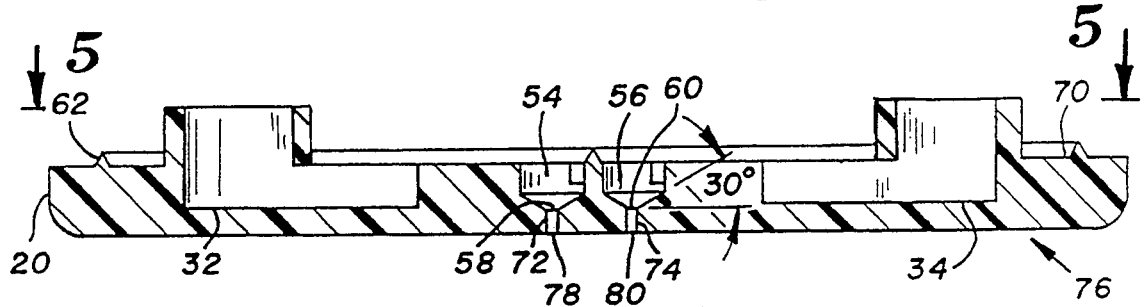
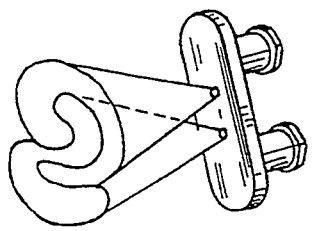
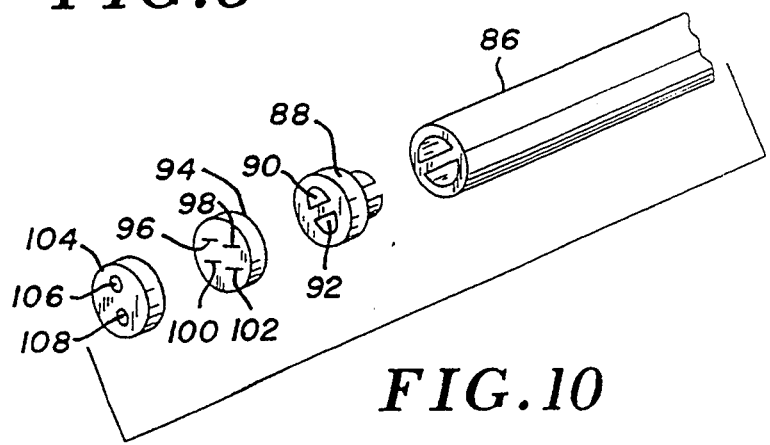

SPRAYER ASSEMBLY FOR PHYSIOLOGIC GLUE

This is a continuation of application Ser. No. 07/809,885, filed Dec. 18, 1991.

BACKGROUND OF THE INVENTION

I. Field of the Invention

This invention relates generally to the design of an improved delivery system for applying adhesives. More particularly, the delivery system includes a novel sprayer assembly for combining adhesives which are stored separately as fluids then applied to a surface as a spray or stream. Although useful for any adhesive made from at least one solution, the delivery system is useful for combining tissue adhesive components such as a first solution of fibrinogen and a second solution of thrombin. Upon contact with one another, these two solutions undergo a rapid chemical reaction which causes curing into a functional tissue adhesive. Thus, it is desired to keep these two solutions separately confined until just prior to the time of direct application on a patient and then thoroughly and rapidly mix them for treatment of a wound.

II. Description of the Prior Art

The treatment of wounds on patients typically involves suturing or covering the wound with an external dressing. There are some applications, however, where the external dressing or sutures are not effective or even act as an irritant. In situations such as treatment of internal body cavities, it has been discovered that treatment of the wound with the body's own healing compounds has been very effective in inducing wound closure and subsequent healing. A common treatment takes advantage of the rapid reaction which occurs when a solution of clotting factors, such as fibrinogen, comes into contact with a solution of a catalyst, such as thrombin, to form a complex which acts as a tissue adhesive. This rapid reaction typically commences within 2 seconds after the solutions initially contact one another, and it typically attains a soft set within 10 seconds of contact. A common name for such a complex is fibrin glue.

Prior fibrin glue delivery systems may generally be categorized as utilizing either turbulence within a solution or overlapping contact of airborne sprays to obtain mixing. The apparatus utilized by either of these systems typically includes confining a fibrinogen solution separately from a thrombin solution, then permitting these two solutions to mix either immediately prior to or upon application on a wound. Typically, these solutions are confined within separate syringes prior to mixing.

An example of a delivery system based on the mixing of overlapping jets of airborne particles is provided in U.S. Pat. No. 4,874,368, which was issued on Oct. 17, 1989 to Miller, et al. This device provides an easily manipulated dual syringe apparatus which enables the two solutions to stream from a sprayer and mix upon application over a wound. A connecting clip member is fitted on each of the piston-type plungers inserted into each syringe. The tip of each syringe is fitted with a specially formed needle, bent to receive the initially parallel outflow from each syringe. The bend in each needle redirects the outflow through a hollow plastic sleeve which serves as a retainer for the long, parallel needle tips. These tips extend slightly beyond the distal end of the hollow sleeve. As solution exits each tip, it is propelled into a spray or stream. The trajectories of the sprays partially overlap and begin mixing either while airborne or as they strike the surface being treated. The clotting reaction commences as the solutions contact one another, due to the close positioning of the needle tips, and spray from one tip can come to rest at the orifice of the other. While temporarily not being used as the surgeon is preoccupied with other matters, contaminants from one tip can cause the clotting reaction to propagate retrograde into the confines of the other needle, plugging the system against further use. Also, thoroughness of mixing depends somewhat upon the technique used by the surgeon.

Syringe applicators employing a mixing chamber are directed toward minimizing the contact time of such solutions prior to application. An example of such a system is provided by U.S. Pat. No. 4,978,336, issued on Dec. 18, 1990 to Capozzi, et al. This biological syringe system includes first and second syringes containing individual components of a tissue adhesive. A manifold locks onto the two syringes and receives the output stream from each syringe. Alternatively, these output streams may be delivered to either a conventional needle or an output nose which terminates in a spray outlet. Mixing of the solutions either occurs within the lumen of the needle or within a mixing space provided within the output nose. In either embodiment, the combination is atomized as it is ejected from the device, either at the tip of the needle or by a spray outlet on the output nose, for atomized application to a wound. This device is similar to other available mixing chamber-type devices because the two solutions are introduced into the mixing chamber from initially parallel ports. Thus, the degree of turbulent flow attained is somewhat dependent upon the Reynolds numbers for the solutions, which contribute to the vortices or eddies which are produced within the chamber. It is also affected by the rate at which the solutions are introduced into the chamber. Furthermore, if the syringe plungers are depressed at a very slow rate, the reacting mixture is not evacuated from the system quickly enough and clotting can occur within the output nose or within the mixing chamber. Thus, it has been found that for quickly reacting substances, such as fibrin glue components, it is desired to have a rapid but uniform mixing that is less dependent on the rate at which the user introduces the solutions into the mixing chamber than that attained in the Capozzi, et al. device.

A syringe-type device for applying a tissue adhesive which seeks more thorough mixing of solutions is disclosed in U.S. Pat. No. 4,735,616, issued on Apr. 5, 1988 to Eibl, et al. This device includes parallel syringes mounted within a holding means. The distal tips of the syringes are attached to a connecting head having connecting channels directed at an angle toward a mixing needle. Thus, each solution enters the mixing needle in a stream which is deflected off the side of the needle to enhance mixing. This device lacks a separate chamber in which this mixing can occur and relies upon mixing as the fluid moves along the connecting channel of the needle applicator. The solutions mix due to predictable, Bernoulli-type turbulent eddies created along the walls of the mixing needle. The length of the mixing needle which receives each of the solutions is calculated to permit them to adequately mix upon contact with one another. Since the clotting reaction occurs so quickly, the length of the mixing needle is no longer than necessary to provide adequate mixing. It has also been found with this device that there is a minimum rate at which the plungers must be depressed into the syringes, below which duration of contact within the mixing needle is excessive and permits clotting therein. Thus, it is once again desirable to have a reliable mode of mixing of the solutions which will both permit a minimum duration of contact prior to application to a wound and not be as dependent upon external factors such as the rate of depression of the syringe. Consequently, it is desirable to eliminate any requirement for spraying a premixed solution.

An additional fault which is characteristic of any system in which mixing occurs within the device is that this rapid reaction, once catalyzed, can propagate retrograde through the entire system and into the syringe containing the solution of clotting factors. Thus, forward flow through the device must exceed the rate at which the reaction can propagate in a retrograde manner. Unless the user has been made aware that this can occur, he may be unaware of the minimum rate at which he should depress the syringes to counteract this tendency.

It is accordingly a principle object of the present invention to provide a new and improved physiologic glue delivery system which permits rapid and complete blending of two solutions.

Another object of the present invention is to provide a new and improved method and apparatus for mixing and applying physiologic glue which eliminates the need for mixing within the device, so the clotting reaction cannot plug an exit nozzle or needle and cannot propagate retrograde into either solution syringe.

It is yet another object of the present invention to provide a new and improved method and apparatus for mixing and applying physiologic glue prior to the time that the mixed solutions begin to cure and attain a soft set state.

A further object of the present invention is to provide a new and improved method and apparatus for mixing and applying physiologic glue using a variety of solution reservoirs, including syringe reservoirs, which are either equally or differently sized.

SUMMARY OF THE INVENTION

The foregoing objects and advantages of the invention are achieved by providing a sprayer assembly for a glue delivery system, having at least one solution reservoir attached to an ejection port for spraying the solution on a treatment site. The ejection port atomizes the solution, forming airborne droplets. When a plurality of ports emit different solutions, the droplets contact one another at the surface and react chemically. An exemplary application for which the glue delivery system is useful is the combination of activated clotting factors, such as fibrinogen, and a catalyst, such as thrombin. In the preferred embodiment, the ports for ejection of the two solutions are positioned parallel to one another at a distance adequate to prohibit the spray exiting one port from contaminating the region of the other port. The emitted solutions mix with one another while airborne, thus obviating the requirement for a mixing chamber.

The disposable applicator/sprayer assembly of the present invention affixes to conventional syringe tips and conventional extension tubing, thus it may be used with a large variety of available reservoirs and requires no special apparatus. Turbulence is enhanced within specially constructed delivery wells, so each solution exits the assembly in a turbulent spray. This turbulence enhances the mixing of the two sprays while airborne.

Upon contact of the two sprayed solutions at the site of a wound, a predictable, rapid chemical reaction commences in about 2 seconds. A soft set condition, leading eventually to a hardened clot is attained within 10 seconds. At this point in time, the sprayed solutions are already positioned at their desired placement on a wound.

As indicated above, fibrin glue delivery systems of various types are well known in the prior art. However, none of these systems provides a truly effective way to apply a fibrin glue-based tissue adhesive on a wound surface without the danger that the delivery apparatus will become plugged before application is completed or that the reaction may propagate retrograde through the apparatus to a solution reservoir. The present invention was developed to specifically resolve these limitations inherent in prior art glue delivery systems, as well as provide an inexpensive, disposable applicator that may be used with a wide variety of solution reservoirs, such as syringes, catheters, delivery tubes attached to solution pouches, and the like. Any combination of these reservoirs may be used, permitting use of a greater range of solution concentrations than in the prior art. Also, solutions may be administered one at a time with no danger that the apparatus will become clogged, because residual solutions do not contact one another. Because mixing occurs external to the device, there is no danger that the device will become plugged or that the reaction will propagate retrograde into a solution reservoir.

Other objects of the present invention and many of its attendant advantages will be more readily appreciated as the invention becomes better understood by reference to the following detailed description when considered in connection with the accompanying drawings in which like reference numerals designate like parts throughout.

DESCRIPTION OF THE DRAWINGS

FIG. 5 is an enlarged, bottom view of the sprayer assembly taken along the line 5—5 of FIG. 8;

FIG. 6 is an enlarged, cross-sectioned view of a preferred weld riser used in the present invention;

FIG. 7 is a side view of an alternative embodiment of the present invention;

FIG. 8 is an enlarged, cross-sectioned side view more clearly depicting the spatial arrangement of the various features of the sprayer assembly of the present invention; and FIG. 9 shows a spray pattern resulting from asymmetric ejection ports; and FIG. 10 is an expanded, perspective view of an alternative embodiment of the present invention.

DESCRIPTION OF THE PREFERRED EMBODIMENT

Figure 1:
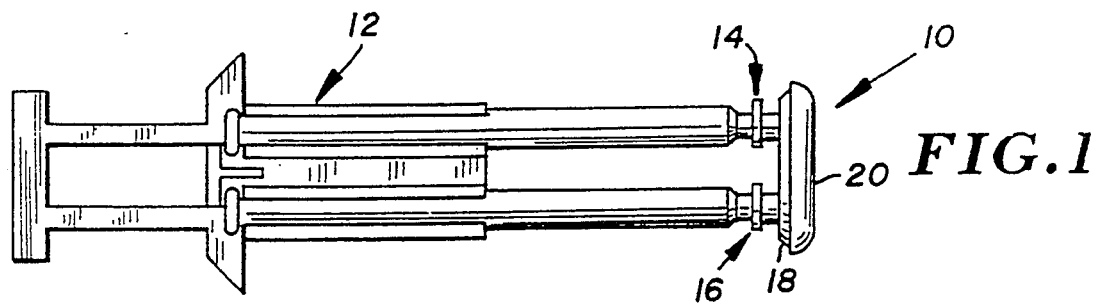
FIG. 1 shows a side view of a preferred embodiment of the present invention.

A preferred embodiment of the sprayer assembly for delivery of fluid components of glue to a treatment site is shown in FIG. 1. In this view, the sprayer assembly 10 is shown attached to a conventional dual-syringed delivery system, generally depicted as 12. The sprayer assembly 10 of the present invention features a pair of conventional Luer-lock connectors 14 and 16 which are preformed extending from a base members or plate 18. The base member 18 is rigidly secured to a sprayer member or plate 20. Although shown attached to a dual-syringed delivery system 12, the container for either solution may be any fluid reservoir, including a catheter or an extension tube joined to any fluid-holding pouch or device. Thus, a pair of solutions may be mixed in a wide variety of concentration ranges and the solutions administered in vastly differing ratios. For example, in one application a ratio of 1:2 of solutions A and B may be desirable, while in another application, a ratio of 1:9 of the same solutions may be desirable. Alternatively, delivery of a desired concentration ratio may be attained by using premixed, standard stock solutions, with which a large volume of one solution may be required in relation to the other.

Figure 2:
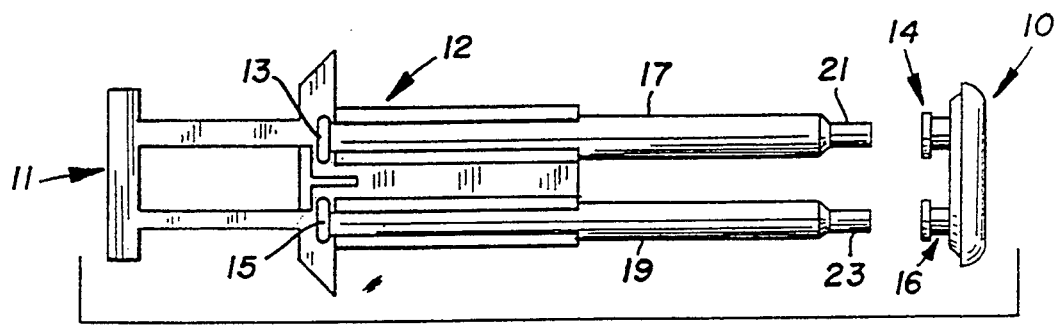
FIG. 2 shows a side view more clearly depicting the attachment of the present invention to a conventional dual syringe fibrin glue delivery system.

FIG. 2 shows an exploded view of the sprayer assembly 10 and the dual syringe delivery system 12. Although connectors 14 and 16 are depicted as Luer-lock connectors, one skilled in the art will readily appreciate that Luer taper connectors will work equally as well for many applications. An example of a dual syringe delivery system 12 compatible with the present invention is provided in U.S. Pat. No. 4,874,368, issued to Miller, et al. As previously discussed, this device includes a connecting clip member 11, which is snapped onto each of a pair of syringe plungers 13 and 15 within conventional syringes 17 and 19, each conventional syringe includes a cylinder.

Figure 3:
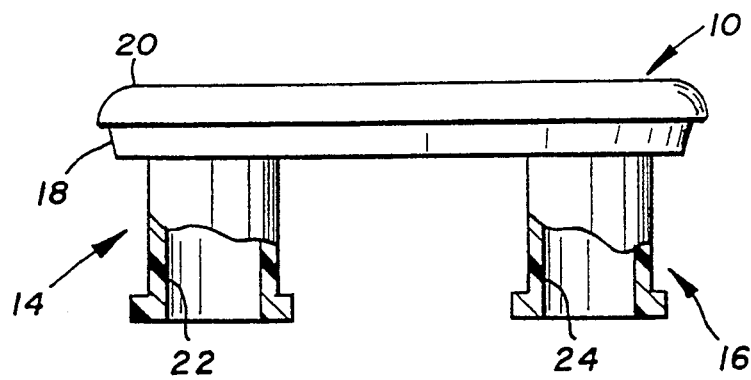
FIG. 3 shows an enlarged, side cut-away view of the sprayer assembly of FIG. 2.

A cut-away, enlarged side view of the sprayer assembly 10 of FIG. 2 is shown in FIG. 3. Proximal syringe receptacles 22 and 24 within Luer-lock connectors 14 and 16 are dimensioned to receive conventional syringe tips 21 and 23, in the known manner. As previously mentioned, although a Luer-lock connection is shown on assembly 10, conventional female receptacles which lack the Luer-lock feature will work equally well for some applications.

One skilled in the art will appreciate that base member 18 may be joined to sprayer member 20 in a variety of ways. For example, these members may be ultrasonically welded, wherein a weld riser (FIG. 6) melts one to the other. Alternatively, these members may either be glued or solvent welded. The material used for the members 18 and 20 may be metal or any thermoplastic or thermosetting material, such as acrylic or ABS material.

Figure 4:
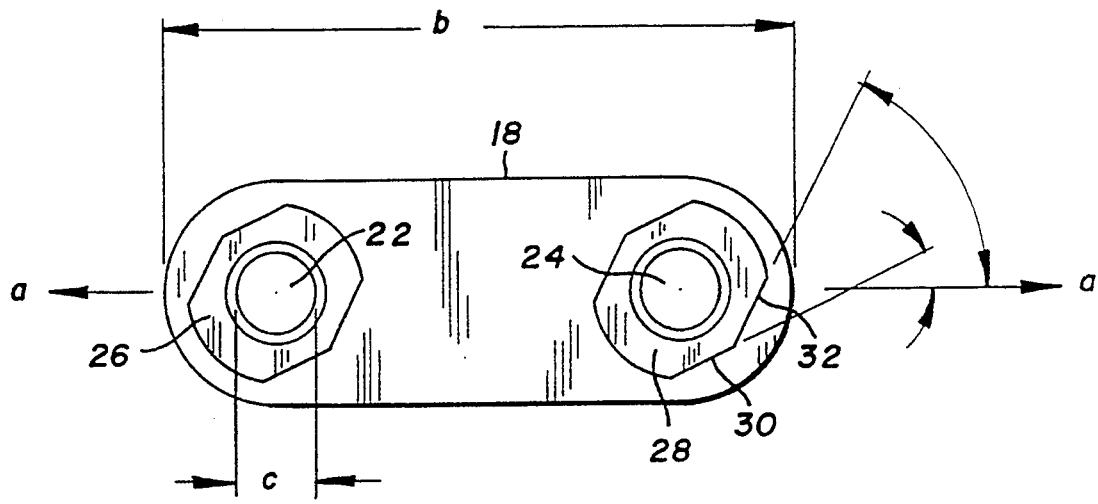
FIG. 4 is a perspective view of the proximal end of the sprayer assembly of FIG. 2.

FIG. 4 shows a proximal end view of the sprayer assembly of FIG. 3, more clearly depicting the Luer connectors. To be adaptable to a wide variety of commercially available syringes, it is suggested that the locking hubs 26 and 28 be preformed in an angular shape. For example, but with no limitation intended, if a longitudinal axis (a—a) is drawn to dissect the syringe receptacles 22 and 24, then one edge of the flange, designated 30, will form a 30° angle with the longitudinal axis a—a. The mirror image of this edge, designated 32, preferably forms a 60° angle with the longitudinal axis (a—a). Both the length of the base unit, generally depicted as b, and the width of the syringe receptacles, generally depicted as c, are dependent upon the size of the syringe selected for use during a particular application. Generally, the length of b is selected to position the receptacles 22 and 24 to receive the syringe tips without straining the syringe barrels, particularly when a pair of syringes of differing sizes are used simultaneously. The width of the receptacle (c) is dimensioned according to the conventional, presently accepted system for sizing commercially available syringes.

Referring again to FIG. 3, and with no limitation to size intended, it is suggested that the distance between the centers of the syringe receptacles 22 and 24, generally designated d, be approximately 0.700 inch. When a Luer-lock connector is used, as shown in FIG. 3, a conventional depth of 0.300 inch is preferred, generally designated e. The depth of the base member 18, generally designated f, is preferably 0.070 inch. The depth of the sprayer assembly, generally designated as g, is preferably 0.065 inch. When a conventional, non-Luer-lock connector is used, it is suggested that the distance between the end of the connector and the seam between the base member 18 and sprayer assembly 20 be approximately 0.060 inch, generally designated as h.

FIG. 5 shows an enlarged, cross-sectioned view of the proximal surface of the sprayer member 20, taken along the line 5—5 of FIG. 3. Shown in shadow are the distal ends of the outwardly extending cylindrical portions on syringe member 20. A pair of Y-shaped channels 34 and 36 each having a trunk portion and two extensions are routed, molded, or otherwise etched or formed into the proximal surface of sprayer member 20. Each extension (38, 40, 42 and 44) of the channels 34 and 36 includes at its end a small connecting channel for the passage of solutions. The connecting channels 46, 48, 50 and 52 each lead to a solution well (54 or 56) where each well includes a larger diameter segment, a funnel segment and a smaller diameter segment. Thus, connecting channel 46 extends from extension 38 to well 54. Similarly, connecting channel 48 extends from extension 40 to well 54. Connecting channel 50 leads from extension 42 and connecting channel 52 leads from extension 44 to well 56. Although the connecting channels 46, 48, 50 and 52 are shown with a side taper of about 15°, one skilled in the art will recognize that any taper between 0° and 90° may be desired to enhance turbulence within the wells 54 and 56. Each well has an exit port 58 and 60, as more clearly shown in FIG. 8.

To assist in affixing the base member 18 to sprayer member 20, a weld riser 62 is formed near the perimeter of sprayer member 20. It also extends between the wells 54 and 56, as shown in FIG. 5. An enlarged cross-section of this weld riser is shown in FIG. 6. Preferably, it forms a sharp peak angled at 45° and extends approximately 0.007 inch from the surface. Alternatively, as shown in FIG. 7, a gasket 64 may be interposed between base member 18 and sprayer member 20. A pair of clips 66 and 68 may be dimensioned to slide over the ends of the sprayer assembly 10 to hold the gasket in place. The clips 66 and 68 may be replaced by a single C-shaped clip (not shown) that fits on the sprayer member 10 between the connectors 14 and 16, without obstructing the orifices from the wells 54 and 56. Suitable materials for these clips are metal or rigid plastic.

FIG. 8 shows an enlarged, cross-sectioned side view of the sprayer member 20, wherein the base member will at 70 abut the weld riser 62 along its entire perimeter when the base and sprayer members are affixed as shown in FIGS. 3 and 7. Each well 54 and 56 extends conically toward an exit port 58 and 60, respectively. A pair of channels 72 and 74 are drilled, molded or otherwise formed from the exterior surface 76 of sprayer member 20 to the exit ports 58 and 60, thus leading to atomizing ejection ports 78 and 80. Each channel is preferably about 0.0150 inch in diameter.

When solution is forced from a syringe or other reservoir 12, it flows within a tip (not shown) securely affixed to a syringe receptacle (22 or 24). It continues to flow along a channel 34 or 36 and into an extension (38, 40, 42 or 44). If it is in extension 38, it continues to flow along connecting channel 46 to well 54. If it is in extension 40, it continues to flow along connecting channel 48 to well 54. If it is in extension 42, it continues to flow along connecting channel 50 to well 56. Similarly, if it is in extension 44, it continues to flow along connecting channel 52 to well 56. Because the connecting channels 46, 48, 50 and 52 are opposably introduced to wells 54 and 56 (FIG. 5), turbulent forces are enhanced within each well. These forces are further enhanced by the conical shape of the distal portions of the wells. With no limitation in size intended, it is suggested that these distal sides slope at a 30° angle with the distal surface 76. Thus, each turbulent solution flows through a well and passes through an exit port (58 or 60) as a vortex. This vortex motion dissipates only minimally as the fluid flows down channels 72 and 74 to atomizing ejection ports 78 and 80, exiting the sprayer member 20 as a swirling spray. Droplets from each ejection port are propelled in a swirling, conical spray which overlaps with the spray from the other port. At the wound site, these sprays or streams are overlaid upon one another and the clotting reaction commences. It continues as unexposed droplets are incorporated into the clot forming on the wound surface, in a manner similar to the manner in which the reaction propagates retrograde to the solution syringe in prior art devices. Thus, the present device avoids the need for internal mixing of the solutions and consequently cannot become clogged by curing of the solutions within the device.

A further advantage of obviating a mixing chamber is that the individual solutions may be laid down on a wound surface one at a time, in any volume or concentration, without danger that residual solution within may cause the reaction to commence within the assembly.

One skilled in the art will recognize that the spray pattern laid upon the wound depends upon the size and shape of ejection ports 78 and 80. FIG. 9 shows the asymmetric pattern 82 and 84 resulting when an oval orifice includes a "V" groove. Any asymmetry or configuration of the orifice will affect the spray pattern produced. Also, a difference in orifice sizes, to accommodate differences in viscosity, will affect the spray pattern produced.

FIG. 10 shows an alternative embodiment of the present invention, dimensioned to be affixed to a catheter 86. In this example, a dual lumen catheter is used, but multiple lumens may be used, just as multiple receptacles may be provided on the sprayer assembly 10. The base member or plate 88, although constructed round instead of oval, includes channels 90 and 92, as provided in base member 18. An intermediate member or plate 94, providing fluid paths 96, 98, 100 and 102 may be interposed between base member 88 and sprayer member or plate 104. Exit ports 106 and 108 are drilled, molded, or otherwise formed in sprayer member 104, analogous to ports 72 and 74 of sprayer member 20. As in the prior embodiment, the sprayer, gasket and base member may individually be comprised of metal or any resilient plastic.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A device for applying to a treatment site a first fluid and a second fluid, which when mixed, revert to a solid state, the first and second fluids being stored and kept separate from each other until dispensed onto the treatment site, the device comprising:

a first syringe for storing and delivering the first fluid, the first syringe having a cylinder for containing the first fluid, a plunger which is movable in the cylinder, and an outlet through which the first fluid is delivered by movement of the plunger within the cylinder;

a second syringe for storing and delivering the second fluid, the second syringe having a cylinder for containing the second fluid, a plunger which is movable in the cylinder, and an outlet through which the second fluid is delivered by movement of the plunger within the cylinder;

a sprayer attachment for spraying the first fluid and the second fluid on to a treatment site, the sprayer attachment including a base plate and a sprayer plate connected together, with a back surface of the base plate sealed to a front surface of the sprayer plate, the base plate having a first receptacle and a second receptacle in a side-by-side arrangement on a front surface of the base plate, the first and second receptacles being attached to the outlets of the first and second syringes, the sprayer plate having a first exit port and a second exit port side-by-side at a back surface of the sprayer plate, the first and second exit ports for dispensing the first and second fluids onto the treatment site, the back surface of the base plate and the front surface of the sprayer plate defining therebetween a first fluid passage which extends from the first receptacle to the first exit port and a second fluid passage which extends from the second receptacle to the second exit port, the first fluid passage including a first fluid channel connected to the first receptacle and a first well connected to the first exit port and the second fluid passage including a second fluid channel connected to the second receptacle and a second well connected to the second exit;

wherein the first fluid channel tangentially connects to the first well and the second fluid channel tangentially connects to the second well.

2. The device in claim 1 wherein the first and second exit ports are spaced so that the first fluid when ejected from the first exit port forms a first spray pattern and the second fluid when ejected from the second exit port from a second spray pattern, the first spray pattern intersecting at least a portion of the second spray pattern.

3. The device in claim 1 wherein the first and second fluid channels are bifurcated.

4. The device in claim 3 wherein the first fluid channel is Y-shaped with a first trunk portion connected to the first receptacle, and a first extension and a second extension connected to the first well, and the second fluid channel is Y-shaped with a second trunk portion connected to the second receptacle, and a third and a fourth extension connected to the second well.

5. The device in claim 4 wherein the first fluid channel includes a first and second connecting channel where the first connecting channel tangentially connects the first extension to the first well, and the second connecting channel tangentially connects the second extension to the first well, and the second fluid channel includes a third and fourth connecting channel where the third connecting channel tangentially connects the third extension to the second well, and the fourth connecting channel tangentially connects the fourth extension to the second well.

6. The device in claim 5 wherein the connecting channels are tapered.

7. The device in claim 6 wherein the first well includes a first funnel segment, and the second well includes a second funnel segment.

8. The device in claim 7 wherein the first well further includes a first larger diameter segment connected to the first and second extensions, and a first smaller diameter segment connected to the first exit port, and wherein the first funnel segment is connected between the first larger diameter segment and the first smaller diameter segment; and the second well further includes a second larger diameter segment connected to the third and fourth extensions, and a second smaller diameter segment connected to the second exit port, and wherein the second funnel segment is connected between the second larger diameter segment and the second smaller diameter segment.

9. The device of claim 8 wherein the first connecting channel is tangentially attached to the first larger diameter segment of the first well and the second connecting channel is tangentially attached to the first larger diameter segment diametrically to the first connecting channel, and the third connecting channel is tangentially attached to the second larger diameter segment of the second well and the fourth connecting channel is tangentially attached to the second larger diameter segment diametrically to the third connecting channel.

10. A sprayer attachment which is attachable to at least two containers for applying to a treatment site first and second fluids, which when mixed, revert to a solid state, the first and second fluids being stored in the first and second containers, respectively, and kept separate from each other until dispensed onto the treatment site, the first and second containers having outlets through which the first and second fluids, respectively, are dispensed under pressure, the sprayer attachment comprising a base plate and a sprayer plate connected together with a back surface of the base plate sealed to a front surface of the sprayer plate, the base plate having a first receptacle and a second receptacle in a side-by-side arrangement on a front surface of the base plate, the first and second receptacles being configured for attachment to the outlets of first and second containers, respectively, the sprayer plate having a first exit port and a second exit port side-by-side at a back surface of the sprayer plate, the first and second exit ports for dispensing the first and second fluids onto the treatment site, the back surface of the base plate and the front surface of the sprayer plate defining therebetween a first fluid passage which extends from the first receptacle to the first exit port and a second fluid passage which extends from the second receptacle to the second exit port, the first fluid passage including a first fluid channel connected to the first receptacle and a first well connected to the first exit port and the second fluid passage including a second fluid channel connected to the second receptacle and a second well connected to the second exit wherein the first fluid channel tangentially connects to the first well and the second fluid channel tangentially connects to the second well.

11. The sprayer attachment of claim 10 wherein the first and second exit ports are spaced so that the first fluid when ejected from the first exit port forms a first spray pattern and the second fluid when ejected from the second exit port forms a second spray pattern, the first spray pattern intersecting at least a portion of the second spray pattern.

12. The device in claim 10 wherein the first and second fluid channels are bifurcated, and the first fluid channel is Y-shaped with a first trunk portion connected to the first receptacle, and a first extension and a second extension connected to the first well, and the second fluid channel is Y-shaped with a second trunk connected to the second receptacle, and a third extension and a fourth extension connected to the second well.

13. The device in claim 12 wherein the first fluid channel includes a first and second tapered connecting channel where the first tapered connecting channel connects the first extension to the first well, and the second tapered connecting channel connects the second extension to the first well, and the second fluid channel includes a third and fourth tapered connecting channel where the third tapered connecting channel connects the third extension to the second well, and the a fourth tapered connecting channel connects the fourth extension to the second well.

14. The device in claim 13 wherein the first well includes a first funnel segment, and the second well includes a second funnel segment.

15. The device in claim 14 wherein the first well further includes a first larger diameter segment connected to the first and second extensions, and a first smaller diameter segment connected to the first exit port, and wherein the first funnel segment is connected between the first larger diameter segment and the first smaller diameter segment; and the second well further includes a second larger diameter segment connected to the third and fourth extensions, and a second smaller diameter segment connected to the second exit port, and wherein the second funnel segment is connected between the second larger diameter segment and the second smaller diameter segment.

16. A device for applying to a treatment site first and second fluids, which when mixed, revert to a solid state, the first and second fluids being stored and kept separate from each other until dispensed onto the treatment site, the device comprising:

a first syringe for storing and delivering the first fluid, the first syringe having a cylinder for containing the first fluid, a plunger which is movable in the cylinder, and an outlet through which the first fluid is delivered by movement of the plunger within the cylinder;

a second syringe for storing and delivering the second fluid, the second syringe having a cylinder for containing the second fluid, a plunger which is movable in the cylinder, and an outlet through which the second fluid is delivered by movement of the plunger within the cylinder;

a sprayer attachment for spraying the first fluid and the second fluid on to a treatment site, the sprayer attachment formed by a plurality of plates sealed together to define first and second passages, including a frontmost plate, the frontmost plate having a first receptacle and second receptacle in a side-by-side side arrangement on a front surface of the frontmost plate, the first and second receptacles being attached to the outlets of the first and second syringes, the rearmost plate having a first exit port and a second exit port side-by-side at a back surface of the rearmost plate, wherein the first fluid passage extends from the first receptacle to the first exit port and the second fluid passage extends from the second receptacle to the second exit port, the first fluid passage including a first fluid channel connected to the first receptacle and a first well connected to the first exit port and the second fluid passage including a second fluid channel connected to the second receptacle and a second well connected to the second exit, wherein the first fluid channel tangentially connects to the first well and the second fluid channel tangentially connects to the second well.

17. The sprayer attachment of claim 16 wherein the first and second exit ports are spaced so that the first fluid when ejected from the first exit port forms a first spray pattern and the second fluid when ejected from the second exit port forms a second spray pattern, the first spray pattern intersecting at least a portion of the second spray pattern.

18. The device in claim 16 wherein the first and second fluid channels are bifurcated.

19. A sprayer attachment which is attachable to at least two containers for applying to a treatment site first and second fluids, which when mixed, revert to a solid state, the first and second fluids being stored in the first and second containers respectively, and kept separate from each other until dispensed onto the treatment site, the first and second containers having outlets through which the first and second fluids respectively are dispensed under pressure, tile sprayer attachment formed by a plurality of plates sealed together to define first and second fluid passages, including a frontmost plate and a rearmost plate, the frontmost plate having a first receptacle and a second receptacle in a side-by-side arrangement on a front surface of the frontmost plate, the first and second receptacles being configured for attachment to the outlets of the first and second containers, the rearmost plate having a first exit port and a second exit port side-by-side at a back surface of the rearmost plate, wherein the first fluid passage extends from the first receptacle to the first exit port and the second fluid passage extends from the second receptacle to the second exit port, the first fluid passage including a first fluid channel connected to the first receptacle and a first well connected to the first exit port and the second fluid passage including a second fluid channel connected to the second receptacle and a second well connected to the second exit, wherein the first fluid channel tangentially connects to the first well and the second fluid channel tangentially connects to the second well.

20. The sprayer attachment of claim 19 further comprising an intermediate plate connected therebetween the back surface of the frontmost plate and the front surface of the rearmost plate.

21. The device of claim 19 wherein the first and second fluid channels are bifurcated.

* * * * *

UNITED STATES PATENT AND TRADEMARK OFFICE
CERTIFICATE OF CORRECTION

PATENT NO. : 5,368,563

DATED : November 29, 1994

INVENTOR(S) : ALAN LONNEMAN, CURTIS H. MILLER

It is certified that error appears in the above-indentified patent and that said Letters Patent is hereby corrected as shown below:

Col. 5, line 5, delete "base members", insert --base member--

Col. 8, line 62, delete "from", insert --forms--

Signed and Sealed this

Fourth Day of April, 1995

Attest:

BRUCE LEHMAN

*Attesting Officer*     *Commissioner of Patents and Trademarks*